(12) United States Patent
Boone

(10) Patent No.: US 10,858,304 B1
(45) Date of Patent: Dec. 8, 2020

(54) AROMATIC ENOL ETHERS

(71) Applicant: Eastman Chemical Company, Kingsport, TN (US)

(72) Inventor: Matthew Allen Boone, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/559,842

(22) Filed: Sep. 4, 2019

(51) Int. Cl.
| | |
|---|---|
| C07C 43/00 | (2006.01) |
| C07C 43/215 | (2006.01) |
| C07C 43/166 | (2006.01) |
| C07C 43/23 | (2006.01) |
| C07C 43/205 | (2006.01) |
| C07C 43/178 | (2006.01) |
| C07C 57/03 | (2006.01) |

(52) U.S. Cl.
CPC .......... *C07C 43/215* (2013.01); *C07C 43/166* (2013.01); *C07C 43/1787* (2013.01); *C07C 43/2055* (2013.01); *C07C 43/23* (2013.01); *C07C 57/03* (2013.01)

(58) Field of Classification Search
CPC . C07C 43/215; C07C 43/166; C07C 43/1787; C07C 43/23
See application file for complete search history.

(56) References Cited

U.S. PATENT DOCUMENTS

| | | |
|---|---|---|
| 2,578,724 A | 12/1951 | Mertzweiller |
| 4,839,413 A | 6/1989 | Kiehlbauch et al. |
| 4,927,876 A | 5/1990 | Coogan et al. |
| 4,939,233 A | 7/1990 | Jenkins et al. |
| 4,946,932 A | 8/1990 | Jenkins |
| 5,053,556 A | 10/1991 | Ohnishi |
| 5,137,961 A | 8/1992 | Goos et al. |
| 5,247,040 A | 9/1993 | Amick et al. |
| 5,296,530 A | 3/1994 | Bors et al. |
| 5,484,849 A | 1/1996 | Bors et al. |
| 6,451,380 B1 | 9/2002 | Speece, Jr. et al. |
| 6,743,748 B2 | 6/2004 | Mizuno et al. |
| 7,208,545 B1 | 4/2007 | Brunner et al. |
| 9,932,486 B1 | 4/2018 | Cogar et al. |
| 2009/0035696 A1 | 2/2009 | Matsuoka |
| 2009/0076311 A1 | 3/2009 | Sato et al. |
| 2012/0289721 A1 | 11/2012 | End et al. |
| 2015/0239816 A1 | 8/2015 | Zaragoza Doerwald et al. |

FOREIGN PATENT DOCUMENTS

| | | |
|---|---|---|
| EP | 0 492 847 A2 | 7/1992 |
| WO | WO 2007/094922 A2 | 8/2007 |

OTHER PUBLICATIONS

Kluge et al. Phosphonate Reagents for the Synthesis of Enol Ethers and One-Carbon Homologation to Aldehydes. Journal of Organic Chemistry, vol. 44, No. 25, pp. 4847-4852. (Year: 1979).*
Co-pending U.S. Appl. No. 16/559,871, filed Sep. 4, 2019; Boone.
Co-pending U.S. Appl. No. 16/559,887, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,977, filed Sep. 4, 2019; Boone.
Co-pending U.S. Appl. No. 16/559,988, filed Sep. 4, 2019; Boone et al.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.

(Continued)

*Primary Examiner* — Sikarl A Witherspoon
(74) *Attorney, Agent, or Firm* — Matthew W. Smith

(57) ABSTRACT

Disclosed are novel aromatic enol ethers. The aromatic enol ethers exhibit low volatile organic content and are reactive film-hardening compounds. The aromatic enol ethers are useful in a variety of chemical applications. The aromatic enol ethers can be used in applications as plasticizers, diluents, wetting agents, coalescing aids and as intermediates in chemical processes. The aromatic enol ethers also have utility as film-hardening additives for coating formulations.

10 Claims, No Drawings

(56) References Cited

OTHER PUBLICATIONS

Moszner, N. et al.; "Reaction behavior of monomeric B-ketoesters. 2. Synthesis, characterization and polymerization of methacrylate group containing enamines;" Polymer Bulletin; 32; pp. 419-426; (1994).
Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.
Robinson, M. et al.; "Epoxide ring-opening and Meinwald rearrangement reactions of epoxides catalyzed by mesoporous aluminosilicates;" Organic & Biomolecular Chemistry; 2009; 7; pp. 2559-2564.
Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.
Smith, O.W. et al.; "New vinyl ester monomers for emulsion polymers;" Progress in Organic Coatings; 22; 1993; pp. 19-25.
Sokolowski, A. et al.; "Acetals and Ethers. Part IV. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.
Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, TENS; 1981; pp. 491-507.
USPTO Notice of Allowance dated Nov. 1, 2019 received in co-pending U.S. Appl. No. 16/559,977.
USPTO Notice of Allowance dated Dec. 10, 2019 received in co-pending U.S. Appl. No. 16/559,977.
USPTO Notice of Allowance dated Nov. 1, 2019 received in co-pending U.S. Appl. No. 16/559,988.
USPTO Notice of Allowance dated Dec. 11, 2019 received in co-pending U.S. Appl. No. 16/559,988.
USPTO Office Action dated Apr. 30, 2020 received in co-pending U.S. Appl. No. 16/560,161.
Trost et al.; "Model for Asymmetric Induction in the Diels-Alder Reaction;" Journal of the American Chemical Society; vol. 102; 1980; pp. 7595-7596.
USPTO Office Action dated Jun. 1, 2020 received in co-pending U.S. Appl. No. 16/559,897.
USPTO Office Action dated Jun. 10, 2020 received in co-pending U.S. Appl. No. 16/559,871.
USPTO Office Action dated Jun. 10, 2020 received in co-pending U.S. Appl. No. 16/559,912.
USPTO Notice of Allowance dated Jun. 24, 2020 received in co-pending U.S. Appl. No. 16/559,887.

\* cited by examiner

AROMATIC ENOL ETHERS

FIELD OF THE INVENTION

This application relates to chemistry generally. In particular, this application relates to enol ethers and more particularly to aromatic enol ethers.

BACKGROUND OF THE INVENTION

Enol ethers are useful in a variety of chemical applications such as plasticizers, diluents, wetting agents and paint additives and as intermediates in chemical processes. Plasticizers, diluents, wetting agents and paint additives often are volatile and evaporate into the atmosphere during use. For example, coalescing aids that are added to water-based paints, act as temporary plasticizers in latex emulsions. The coalescing aids lowers the glass transition temperature (Tg) of the latex polymer and as the paint dries, the polymers that have been softened by the coalescing aid are allowed to flow together and form a film after the water has left the system. Coalescing aids that are volatile evaporate out of the film. This allows the polymer to return to the original Tg thereby giving harder films for better block and print resistant coatings. Due to environmental concerns, the use of volatile materials such as paint additives, plasticizers, diluents, wetting agents and coalescing aids are increasing undesirable.

As a result, there is a need for materials that can be used as plasticizers, diluents, wetting agents, and paint additives that exhibit low volatility.

SUMMARY OF THE INVENTION

The invention is set forth in the appended claims.

The present application relates to an enol ether compound according to Formula I:

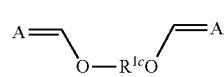

I wherein:

A is

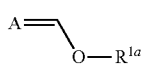, wherein ** indicates the point of attachment, and $R^{1a}$ is

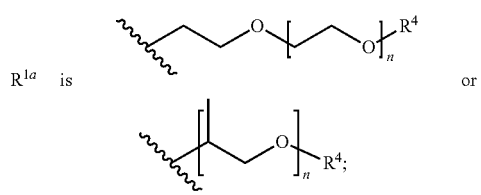

each $R^2$ is independently $(C_{5-10})$aryl;
each $R^3$ is independently $(C_{1-10})$alkyl or $(C_{5-10})$aryl;
$R^4$ is hydrogen, $(C_{1-12})$alkyl, $(C_{2-12})$alkenyl, or —C(O)$R^5$;

$R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
n is an integer from 1 to 15.

The present application also relates to an enol ether compound according to Formula II:

II wherein:
each A is independently

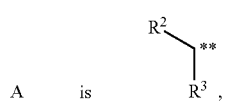, wherein ** indicates the point of attachment, and;

$R^{1c}$ is

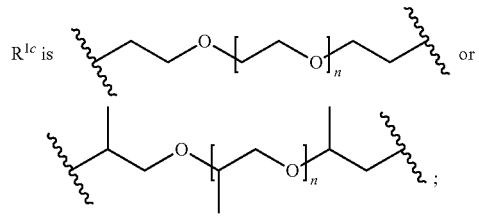

each $R^2$ is independently $(C_{5-10})$aryl;
each $R^3$ is independently $(C_{1-10})$alkyl or $(C_{5-10})$aryl; and
n is an integer from 1 to 15.

The present application also discloses compositions made from the compounds according to Formula I and II, and processes for preparing enol ethers.

DETAILED DESCRIPTION

Definitions

In this specification and in the claims that follow, reference will be made to a number of terms, which shall be defined to have the following meanings.

"Alkyl" means an aliphatic hydrocarbon. The alkyl can specify the number of carbon atoms, for example $(C_{1-5})$ alkyl. Unless otherwise specified, the alkyl group can be unbranched or branched. In some embodiments, the alkyl group is branched. In some embodiments, the alkyl group is unbranched. Non-limiting examples of alkanes include methane, ethane, propane, isopropyl (i.e., branched propyl), butyl, and the like.

"Alkenyl" means an aliphatic hydrocarbon with one or more unsaturated carbon-carbon bonds. The alkenyl can specify the number of carbon atoms, for example $(C_{2-12})$ alkenyl. Unless otherwise specified, the alkyl group can be unbranched or branched. In some embodiments, the alkyl group is branched. In some embodiments, the alkyl group is unbranched. Non-limiting examples of alkanes include ethenyl, propenyl, butenyl, hexa-3,5-dienyl, and the like.

"Alcohol" means a chemical containing one or more hydroxyl groups.

"Aldehyde" means a chemical containing one or more —C(O)H groups.

"Cycloalkyl" means a cyclic hydrocarbon compound. The cycloalkyl can specify the number of carbon atoms in ring system, for example $(C_{3-8})$cycloalkyl. Non-limiting examples of cycloalkyl include cyclopropyl, cyclobutyl, cyclohexyl, and cyclooctyl.

"Aryl" means a ring system made up carbon atoms that has at least one ring that is aromatic. The carbon units making up the aryl ring may be specified, for example 5- to 9-membered aryl. Non-limiting examples of aryl include phenyl, naphthyl, 2,3-dihydro-1H-indene, and 1,2,3,4-tetrahydronaphthalene.

Values may be expressed as "about" or "approximately" a given number. Similarly, ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C; or a combination of A and B, A and C, B and C, or A, B, and C.

Presented herein are novel enol ethers which can be used in applications such as (but not limited to) plasticizers, diluents, wetting agents, coalescing aids and paint additives.

In some embodiments the invention is a compound according to Formula I:

I wherein:

A is $\overset{R^2}{\underset{R^3}{\diagdown}}$, wherein  indicates the point of attachment, $R^{1a}$ is a group with —O—($CH_2CH_2O$)$_n$—$R^4$ or branched form with $R^4$;

$R^2$ is $(C_{5-10})$aryl; $R^3$ is $(C_{1-10})$alkyl or $(C_{5-10})$aryl; $R^4$ is hydrogen, $(C_{1-12})$alkyl, $(C_{2-12})$alkenyl, or —C(O)$R^5$; $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; each $R^6$ is $(C_{1-4})$alkoxy, or oxo; and n is an integer from 1 to 15.

In another embodiment,

A is $\overset{R^2}{\underset{R^3}{\diagdown}}$, wherein  indicates the point of attachment.

In some embodiments, $R^2$ is phenyl, substituted phenyl, naphthyl, substituted napththyl, furanyl, or substituted furanyl. In some embodiments, $R^3$ is methyl, ethyl, propyl, butyl, pentyl, heptyl, hexyl, heptyl, octyl, nonyl, or decyl. In some embodiments, $R^3$ is phenyl, substituted phenyl, naphthyl, substituted napthyl, furanyl, or substituted furanyl. In some embodiments n is an integer from 1 to 4.

In some embodiments, $R^2$ is phenyl or substituted phenyl; and $R^3$ is methyl, ethyl, phenyl, or substituted phenyl. In some embodiments n can be an integer from 1 to 4.

In some embodiments, $R^4$ is —C(O)$R^5$. In some embodiments, $R^5$ can be $(C_{1-12})$alkyl unsubstituted or substituted by $R^6$. In some embodiments, $R^5$ can be $(C_{2-12})$alkenyl unsubstituted or substituted by $R^6$. In some embodiments, $R^5$ can be $(C_{3-8})$cycloalkyl. In some embodiments, $R^5$ can be 5- to 9-membered aryl.

In some embodiments, $R^4$ is hydrogen. In some embodiments, $R^4$ is $(C_{1-12})$alkyl.

In some embodiments, $R^4$ is methyl, ethyl, propyl, butyl, pentyl, hexyl, heptyl, octyl, or nonyl. In some embodiments, $R^4$ is ethyl, propyl, or butyl. In some embodiments, $R^4$ is ethyl or butyl. In some embodiments, $R^4$ is $(C_{2-12})$alkenyl.

In some embodiments, $R^4$ is —C(O)$R^5$. In some embodiments, $R^5$ is $(C_{1-12})$alkyl unsubstituted or substituted by $R^6$. In some embodiments, $R^5$ is methyl, ethyl, propyl, butyl, pentyl, hexyl, heptyl, octyl, or nonyl. In some embodiments, $R^5$ is methyl. In some embodiments, $R^5$ is $(C_{2-12})$alkenyl unsubstituted or substituted by $R^6$.

In some embodiments, $R^5$ is $(C_{3-8})$cycloalkyl. In some embodiments, $R^5$ is cyclobutyl, cyclopenyl, cyclohexyl, cycloheptyl, or cyclooctyl. In some embodiments, $R^5$ is cyclohexyl.

In some embodiments, $R^5$ is a 5- to 9-membered aryl. In some embodiments, $R^5$ is phenyl or naphthyl. In some embodiments, $R^5$ is phenyl.

In some embodiments, n is an integer from 1 to 2. In some embodiments, n is an integer from 1 to 3. In some embodiments, n is an integer from 1 to 4. In some embodiments, n is an integer from 1 to 5. In some embodiments, n is an integer from 1 to 6. In some embodiments, n is an integer from 1 to 7. In some embodiments, n is an integer from 1 to 8. In some embodiments, n is an integer from 1 to 9. In some embodiments, n is an integer from 1 to 10. In some embodiments, n is an integer from 1 to 11. In some embodiments, n is an integer from 1 to 12. In some embodiments, n is an integer from 1 to 13. In some embodiments, n is an integer from 1 to 14. In some embodiments, n is an integer from 1 to 15.

In some embodiments, the compounds of Formula I have a volatile organic content of less than 50 wt % according to ASTM D6886. In some embodiments, the volatile organic content is less than 30 wt %. In embodiments, the volatile organic content is less than 10 wt %. In some embodiments, the volatile organic content is less than 5 wt %. In some embodiments, the volatile organic content is less than 3 wt %. In some embodiments, the volatile organic content is less than 2 wt %. In some embodiments, the volatile organic content is less than 1 wt %. In some embodiments, the volatile organic content is less than 0.8 wt %.

Another embodiment of the invention is an enol ether compound according to Formula II:

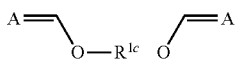

II wherein:
each A is independently

wherein ** indicates the point of attachment, or $R^{1c}$ is

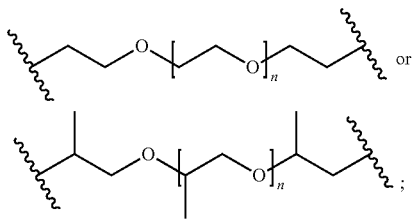

each $R^2$ is independently $(C_{5-10})$aryl; each $R^3$ is independently $(C_{1-10})$alkyl or $(C_{5-10})$aryl; and n is an integer from 1 to 15.

In some embodiments, each

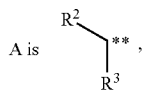

wherein ** indicates the point of attachment. In some embodiments of this invention, n is an integer 1 to 3.

In some embodiments, $R^2$ is phenyl, substituted phenyl, naphthyl, substituted napththyl, furanyl, or substituted furanyl. In some embodiments, $R^3$ is methyl, ethyl, propyl, butyl, pentyl, heptyl, hexyl, heptyl, octyl, nonyl, decyl, phenyl, substituted phenyl, naphthyl, substituted napththyl, furanyl, or substituted furanyl. In some embodiments, n is an integer from 1 to 3.

In some embodiments, $R^2$ is phenyl or substituted phenyl; and $R^3$ is methyl, ethyl, phenyl, or substituted phenyl. In some embodiments, n is an integer from 1 to 3.

In some embodiments, $R^2$ is butyl; and $R^3$ is ethyl. In some embodiments, n is an integer from 1 to 3.

In some embodiments, n is an integer from 1 to 2. In some embodiments, n is an integer from 1 to 3. In some embodiments, n is an integer from 1 to 4. In some embodiments, n is an integer from 1 to 5. In some embodiments, n is an integer from 1 to 6. In some embodiments, n is an integer from 1 to 7. In some embodiments, n is an integer from 1 to 8. In some embodiments, n is an integer from 1 to 9. In some embodiments, n is an integer from 1 to 10. In some embodiments, n is an integer from 1 to 11. In some embodiments, n is an integer from 1 to 12. In some embodiments, n is an integer from 1 to 13. In some embodiments, n is an integer from 1 to 14. In some embodiments, n is an integer from 1 to 15.

In some embodiments, the compound of Formula II has a volatile organic content of less than 50 wt % according to ASTM D6886. In one class of this embodiment, the volatile organic content is less than 30 wt %. In one class of this embodiment, the volatile organic content is less than 10 wt %. In one class of this embodiment, the volatile organic content is less than 5 wt %. In one class of this embodiment, the volatile organic content is less than 3 wt %. In one class of this embodiment, the volatile organic content is less than 2 wt %. In one class of this embodiment, the volatile organic content is less than 1 wt %. In one class of this embodiment, the volatile organic content is less than 0.8 wt %.

Compositions

The enol ether compounds disclosed in the present application exhibit a low volatile organic content (less than 50 wt %, but as low as 0.7 wt % according to ASTM D6886). The enol ethers can be used as reactive film-hardening compounds. Reactive film-hardening compounds react with components in coating compositions to form crosslinks in the films providing improved film properties. When we say that the enol ether compounds of this invention can be used as reactive film-hardening additives, we mean when added to a coating composition, that a harder film is obtained upon curing the composition than is obtained in the absence of the invention enol ether additives, or that the coating composition exhibits a higher gel fraction than in the absence of the enol ether additive, or that both coating composition hardness and increased gel fraction properties are improved by the addition of the enol ether reactive film-hardening additives.

Not wishing to be bound by any theory, the increase in hardness observed in a coating that contains the enol ether additives described herein may be the result of a chemical reaction, so that the additives described herein may be described as "reactive" enol ether film-hardening additives.

The enol ether materials described herein can also facilitate the individual latex particles coming together to form a continuous film at a given temperature by reducing the minimum film-forming temperature (MFFT) of the latex polymer.

In some embodiments, the composition comprises the compound represented by Formula I. In some embodiments, the composition comprises the compound represented Formula II.

In some embodiments, the compounds of Formula I or II are enol ethers represented by the Formulas 1-26 (a,b):

1
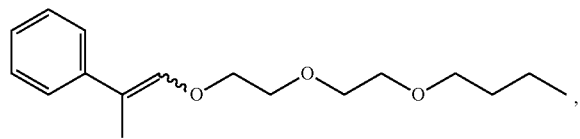
2
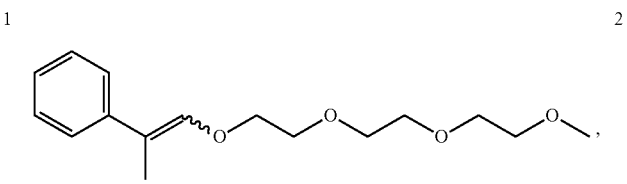
3
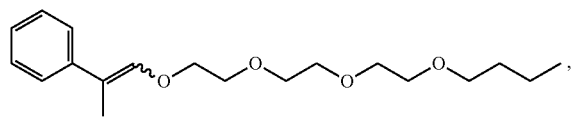
4a
 +
4b
5a
 +
5b
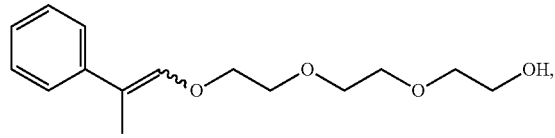
6
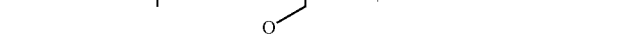
7
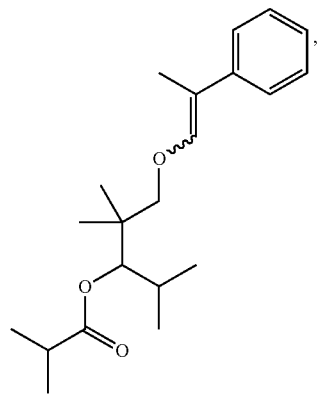
8
9
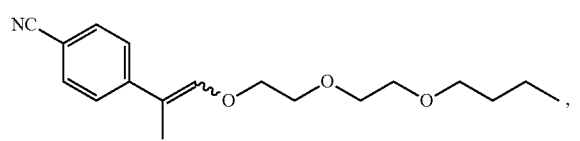
10
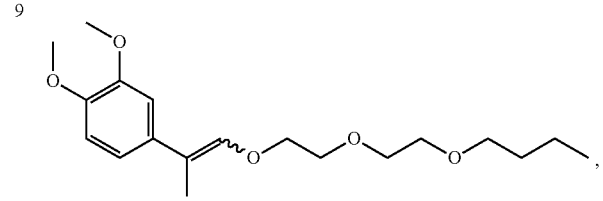

-continued
11
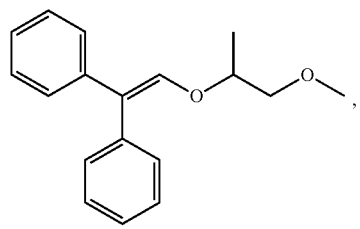
12
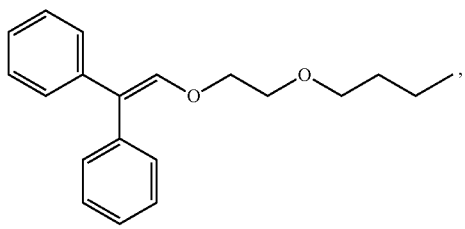
13
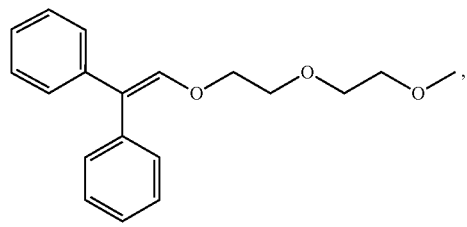
14
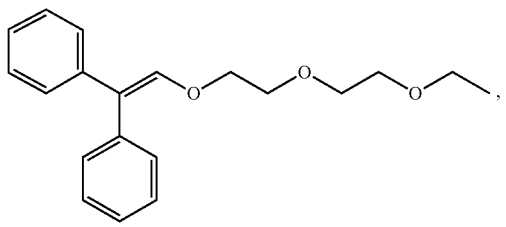
15
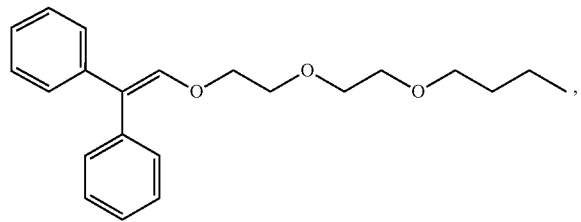
16
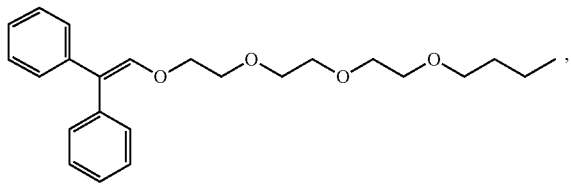
17
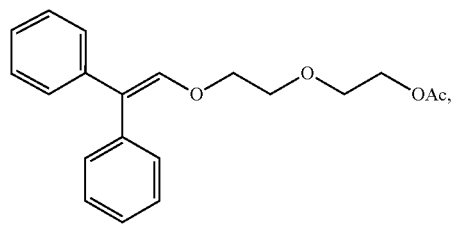
18
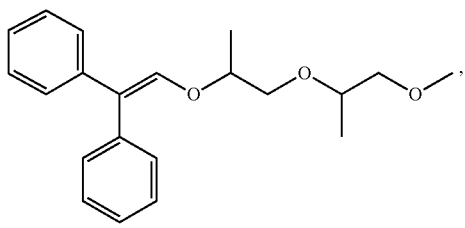
19
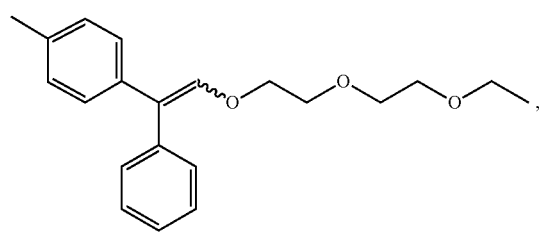
20
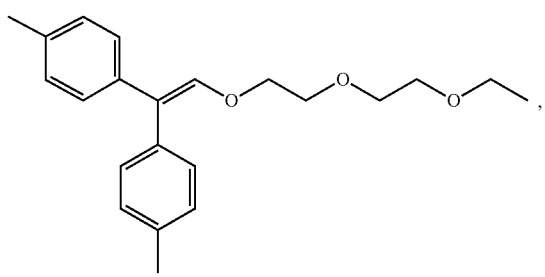
21
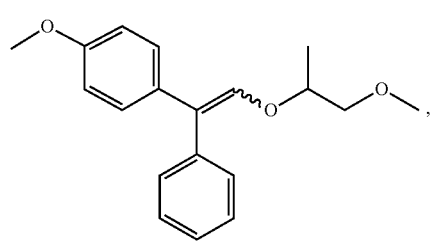
22
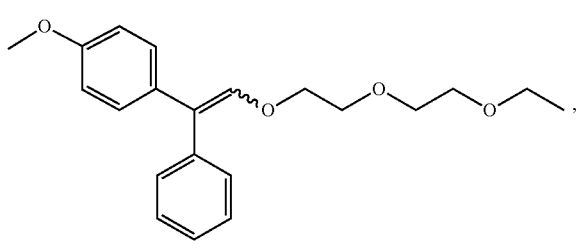

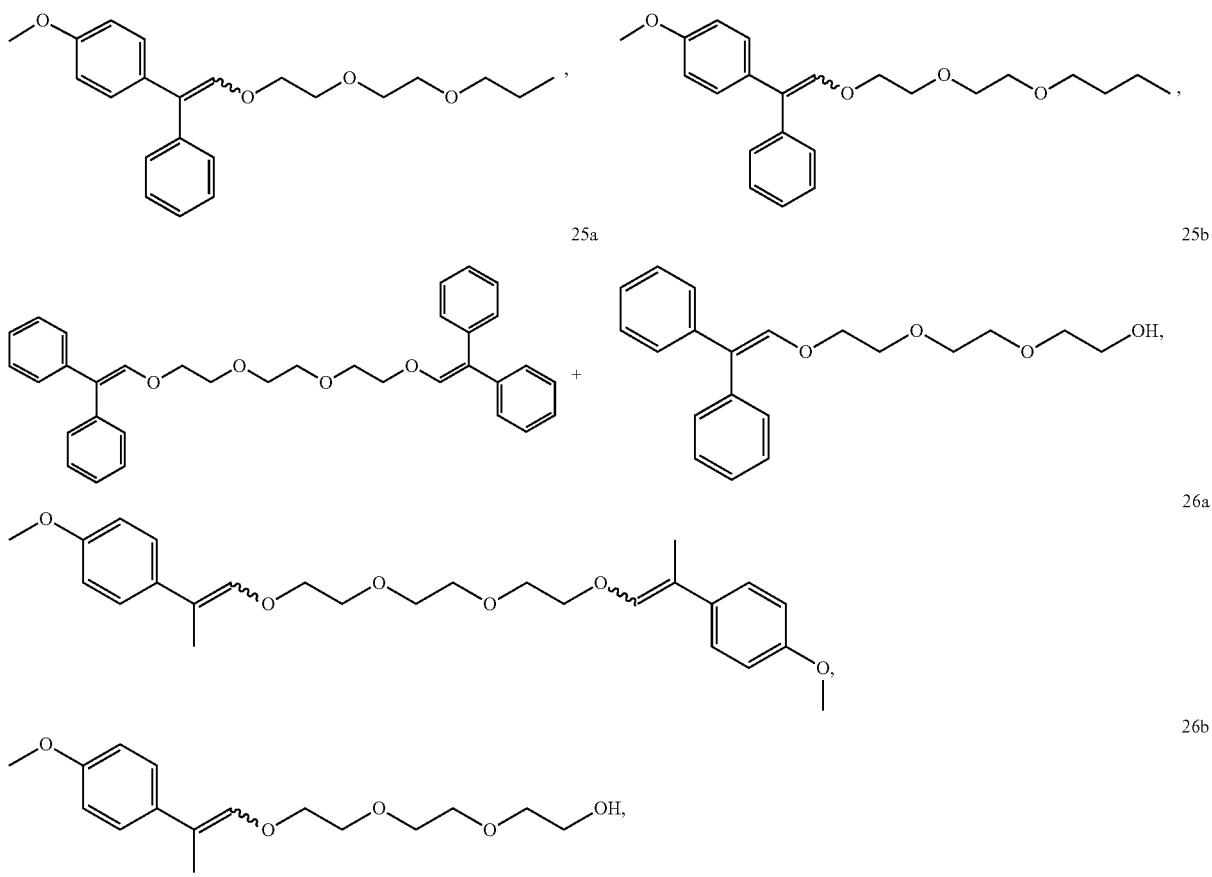

and isomers thereof.

The enol ethers depicted by Formulas 1-26(a,b) are representative of the enol ethers claimed herein. Isomers of the enol ethers depicted by Formulas 1-26(a,b) are expected to be produced during synthesis of the enol ethers depicted by Formulas 1-26(a,b). All isomers of the enol ethers depicted by Formulas 1-26(a,b) and are within the scope of the claims set forth herein.

The compounds depicted by Formula I and II include those having a weight percent volatile content of less than 50%, as measured according to ASTM Method D6886. This test may be conducted generally by heating the sample in a forced air oven at 110° C. for 60 minutes. The weight loss after the test is deemed to result from a loss of volatiles originally present in the sample; the percent volatile present in the original sample may then be calculated. Although the cited test can be conducted on coating compositions containing other components such as latex polymers, the values cited herein may be obtained from a sample of the additive itself. The weight percent volatile of a film-hardening aid may be used herein as a yardstick to measure the amount of VOC the additive would contribute to the VOC in a particular end use such as a component of a coating composition.

EXAMPLES

This invention can be further illustrated by the following examples thereof, although it will be understood that these examples are included merely for purposes of illustration and are not intended to limit the scope of the invention unless otherwise specifically indicated.

Abbreviations:

mL is milliliter; wt % is weight percent; eq is equivalent(s); hrs or h is hour(s); mm is millimeter; m is meter; GC is gas chromatography; ° C. is degree Celsius; min is minute; $t_R$ is retention time; VOC is volatile organic compound; MeP is methyl palmitate; w/v is weight/volume; µL is microliter. RFHA is reactive film-hardening additive.

Example 1: Preparation of (E/Z)-(1-(2-(2-butoxyethoxy)ethoxy)prop-1-en-2-yl)benzene [1]

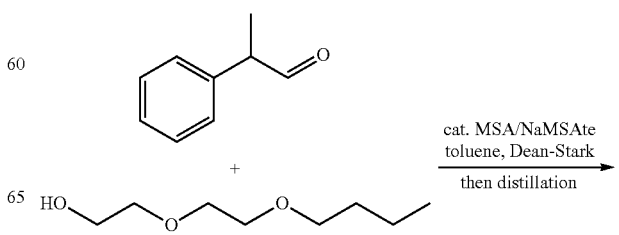

-continued

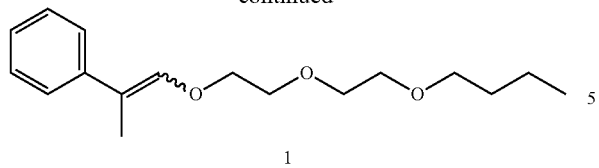

1

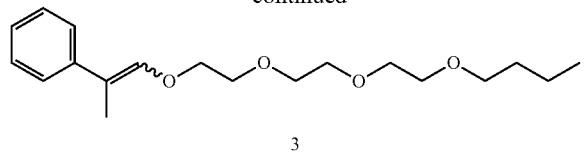

3

Method 1:

2-phenylpropionaldehyde (100 g) was added to a nitrogen-swept, 1 L 4-necked round-bottom flask fitted with overhead-stirrer, thermocouple, and Dean-Stark. Diethyleneglycol monobutyl ether (260 g) was added all at once, followed by the addition of 250 g of toluene. Sodium methanesulfonate (2.20 g) was added to the flask, followed by the addition of methanesulfonic acid (1.21 mL). The reaction was heated to reflux and held at that temperature for 15 hrs. During that time, ca. 13.5 mL of water collected. The toluene was removed under reduced pressure using a rotary evaporator. Then 50% caustic (0.902 mL) was added all at once. The mixture was fractionally distilled under reduced pressure. The product distilled at a vapor temperature of 188° C. at 3 torr. The product was isolated as a mixture of E/Z isomers and was a near colorless oil (164 g, 79% yield). GC-MS (Instrument A) $t_R$: 9.41 min, 9.58 min (Exact mass: 278.1882, found: 278.1882 m/z).

The remaining examples were prepared according to Method 1.

Example 2: Preparation of (E/Z)-13-phenyl-2,5,8,11-tetraoxatetradec-12-ene [2]

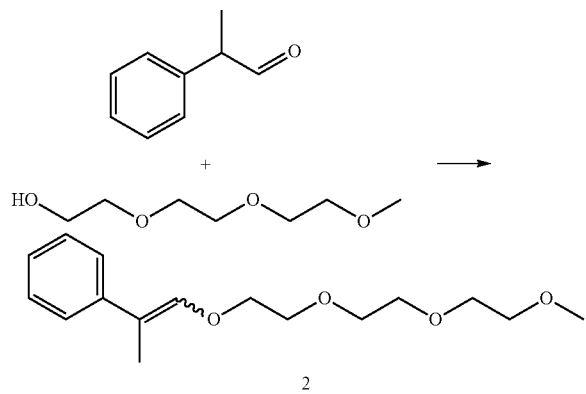

2

GC-MS (Instrument A) $t_R$: 9.54 min, 9.72 min (Exact mass: 280.1675 m/z, found 280.1675 m/z).

Example 3: Preparation of (E/Z)-2-phenyl-4,7,10,13-tetraoxaheptadec-2-ene [3]

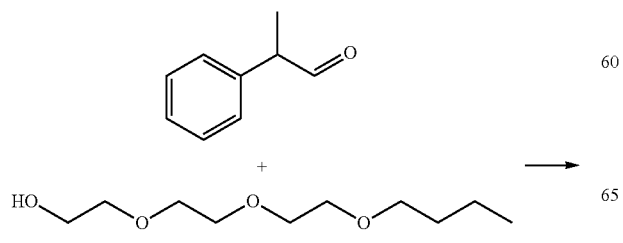

The product enol ether was isolated as a mixture of E/Z isomers and was isolated as a near colorless liquid. GC-MS (Instrument A) $t_R$: 10.49 min, 10.52 min (Exact mass: 322.2144 m/z, found 322.4500 m/z).

Example 4: Preparation of a mixture of (2E/Z, 14E/Z) 2,15-diphenyl-4,7,10,13-tetraoxahexadeca-2,14-diene [4a] and (E/Z)-2-(2-(2-((2-phenyl prop-1-en-1-yl)oxy)ethoxy)ethoxy)ethan-1-ol [4b]

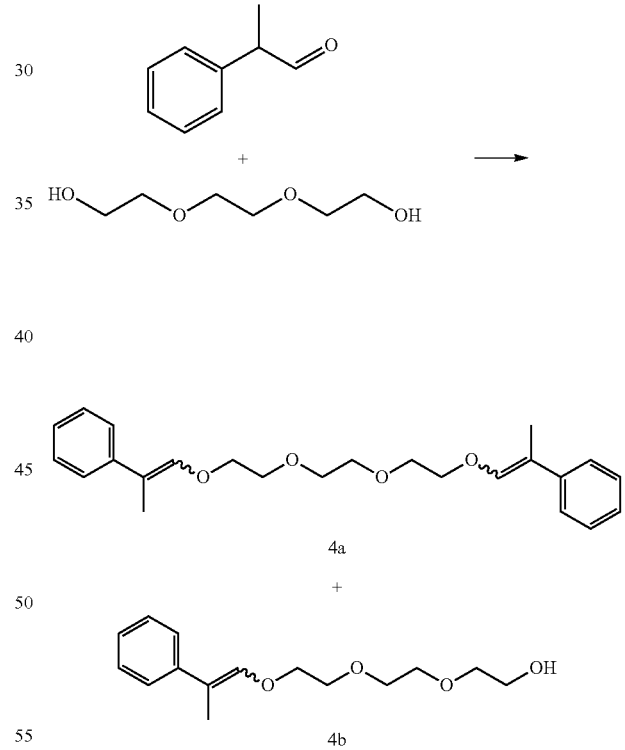

GC-MS (Instrument A) $t_R$: 9.60 min, 9.80 min (Exact mass: 266.1518 m/z, found: 266.1518 m/z), 12.42 min, 12.62 min, 12.84 min (Exact mass: 382.2144 m/z, found: 382.2144 m/z).

Example 5: Preparation of an isomeric mixture of (E/Z)-2,2,4-trimethyl-3-((2-phenylprop-1-en-1-yl)oxy)pentyl isobutyrate [5a] and (E/Z)-2,2,4-trimethyl-1-((2-phenylprop-1-en-1-yl)oxy)pentan-3-yl isobutyrate [5b]

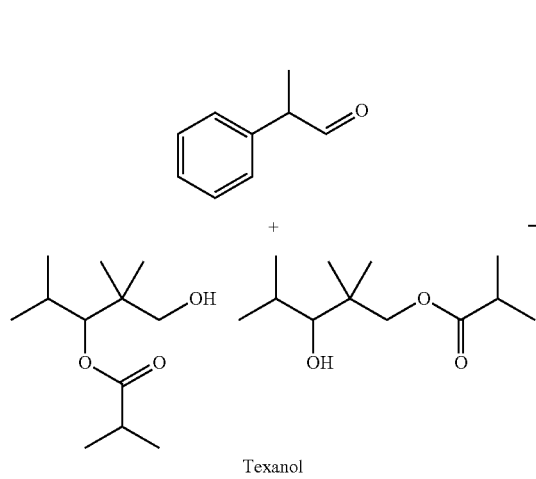

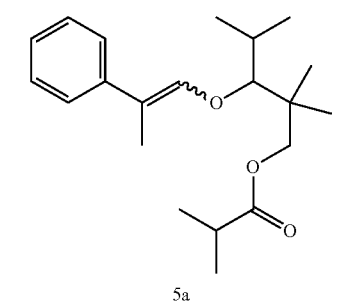

GC-MS (Instrument B) $t_R$: 17.28 min, 17.46 min, 17.69 min, 18.06 min (Exact mass: 332.24 m/z, found: 332.3 m/z).

Example 6: Preparation of (E/Z)-1-(1-(2-(2-ethoxyethoxy)ethoxy)prop-1-en-2-yl)-4-methoxybenzene [6]

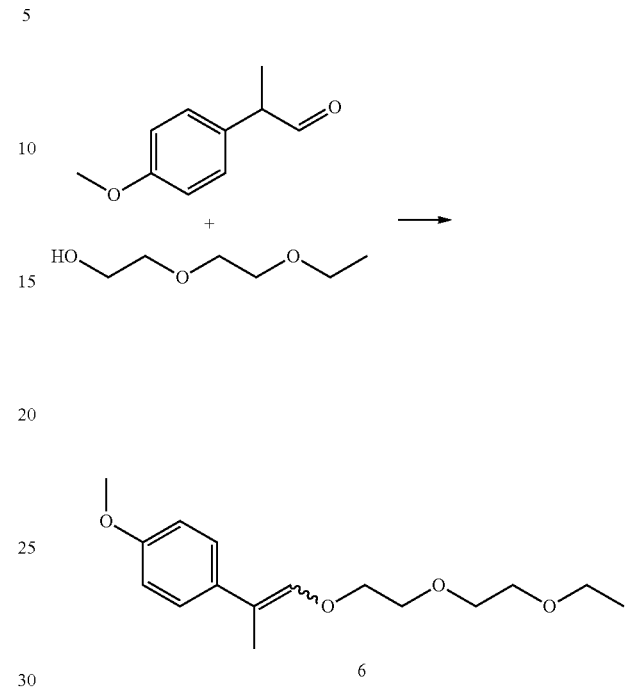

GC-MS (Instrument B) $t_R$: 17.41 min, 17.71 min (Exact mass: 280.17 m/z, found: 280.1 m/z).

Example 7: Preparation of (E/Z)-1-(1-(2-(2-butoxyethoxy)ethoxy)prop-1-en-2-yl)-4-methoxybenzene [7]

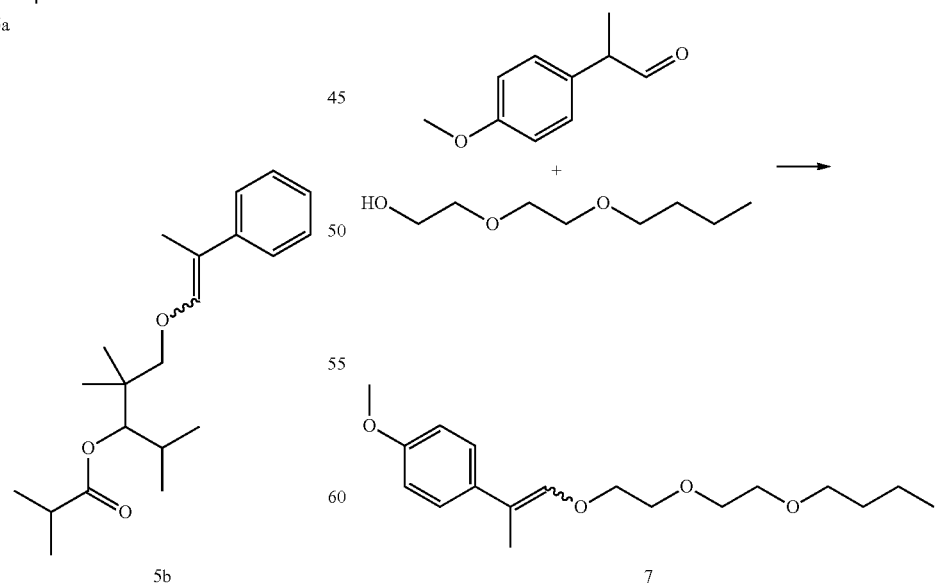

GC-MS (Instrument B) $t_R$: 18.52 min, 18.91 min (Exact mass: 308.20 m/z, found: 308.3 m/z).

Example 8: Preparation of (E/Z)-1-methoxy-4-(1-((1-((1-methoxypropan-2-yl)oxy)propan-2-yl)oxy)prop-1-en-2-yl)benzene [8]

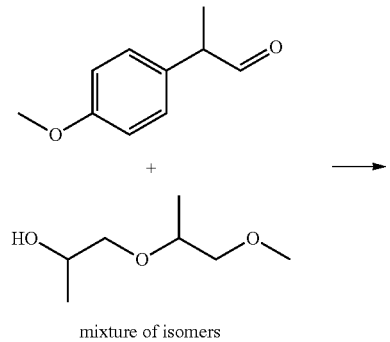

mixture of isomers

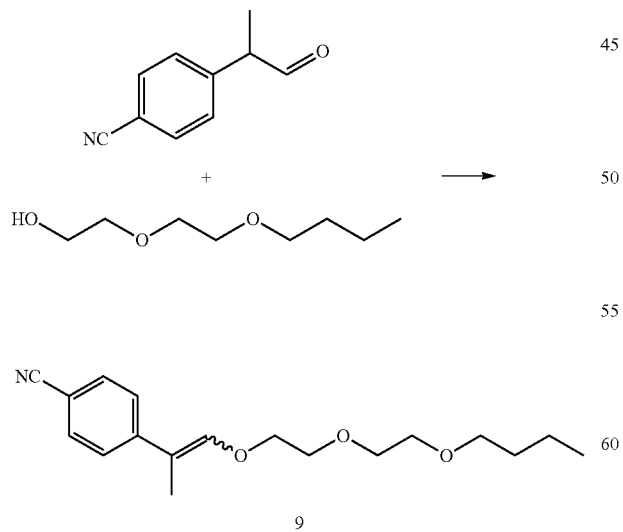

8

GC-MS (Instrument B) $t_R$: 17.09 min, 17.21 min, 17.43 min, 17.55 min (Exact mass: 294.18 m/z, found: 294.1 m/z).

Example 9: Preparation of (E/Z)-4-(1-(2-(2-butoxyethoxy)ethoxy)prop-1-en-2-yl)benzonitrile [9]

9

GC-MS (Instrument B) $t_R$: 19.31 min, 19.75 min (Exact mass: 303.18 m/z, found: 303.1 m/z).

Example 10: Preparation of (E/Z)-4-(1-(2-(2-butoxyethoxy)ethoxy)prop-1-en-2-yl)-1,2-dimethoxybenzene [10]

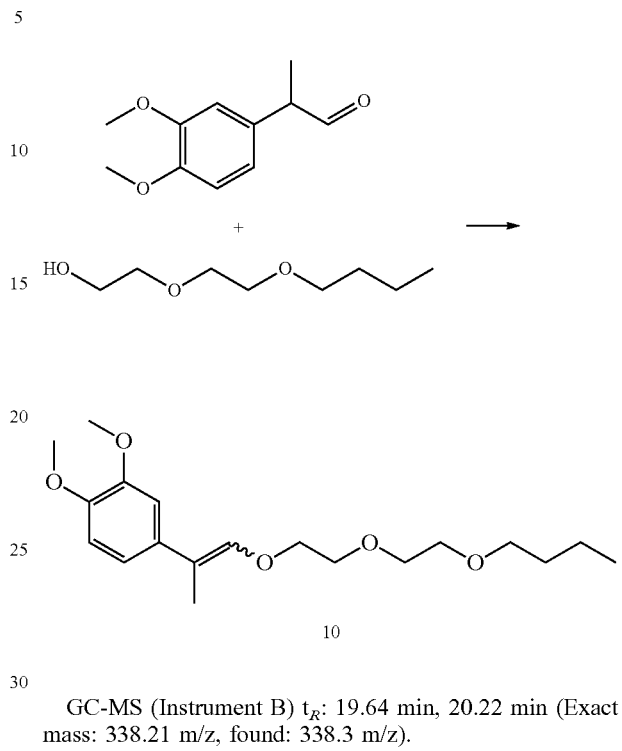

10

GC-MS (Instrument B) $t_R$: 19.64 min, 20.22 min (Exact mass: 338.21 m/z, found: 338.3 m/z).

Example 11: Preparation of (2-((1-methoxypropan-2-yl)oxy)ethene-1,1-diyl)dibenzene [11]

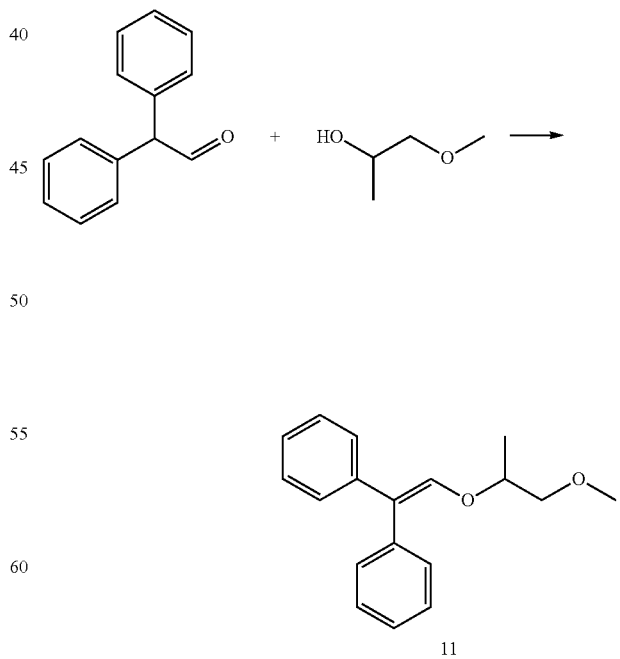

11

GC-MS (Instrument A) $t_R$: 9.41 min (Exact mass: 268.1463, found: m/z=268.1463).

Example 12: Preparation of (2-(2-butoxyethoxy)ethene-1,1-diyl)dibenzene [12]

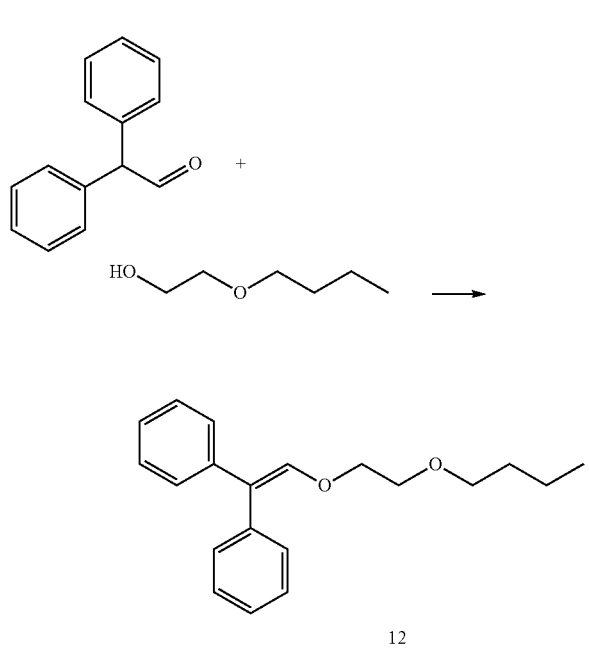

GC-MS (Instrument A) $t_R$: 10.34 min (Exact mass: 296.1776 m/z, found: 296.1776 m/z).

Example 13: Preparation of (2-(2-(2-methoxyethoxy)ethoxy)ethene-1,1-diyl)dibenzene [13]

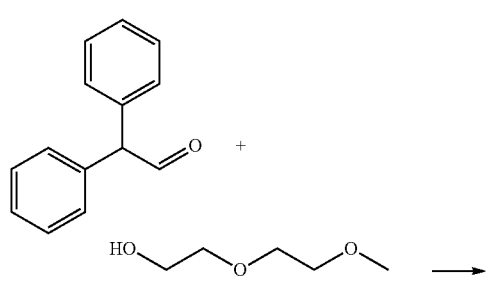

GC-MS (Instrument A) $t_R$: 10.48 min (Exact mass: 298.1569 m/z, found: 298.1569 m/z).

Example 14: Preparation of (2-(2-(2-ethoxyethoxy)ethoxy)ethene-1,1-diyl)dibenzene [14]

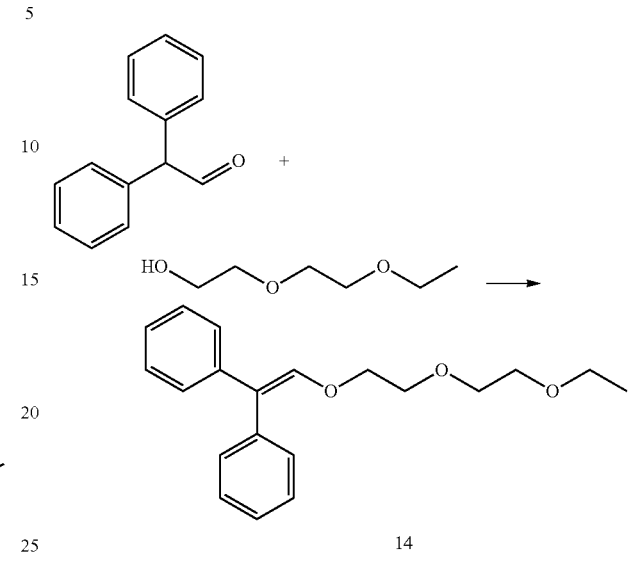

GC-MS (Instrument A) $t_R$: 10.67 min (Exact mass: 312.1725 m/z, found: 312.1725 m/z).

Example 15: Preparation of (2-(2-(2-butoxyethoxy)ethoxy)ethene-1,1-diyl) dibenzene [15]

GC-MS (Instrument A) $t_R$: 11.29 min (Exact mass: 340.2038 m/z, found: 340.2038 m/z).

Example 16: Preparation of 1,1-diphenyl-3,6,9,12-tetraoxahexadec-1-ene [16]

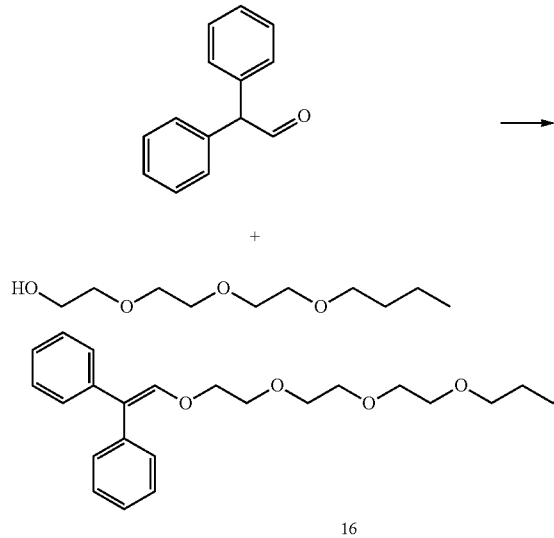

GC-MS (Instrument A) $t_R$: 12.18 min (Exact mass: 384.2301 m/z, found: 384.2301 m/z).

Example 17: Preparation of 2-(2-((2,2-diphenylvinyl)oxy)ethoxy)ethyl acetate [17]

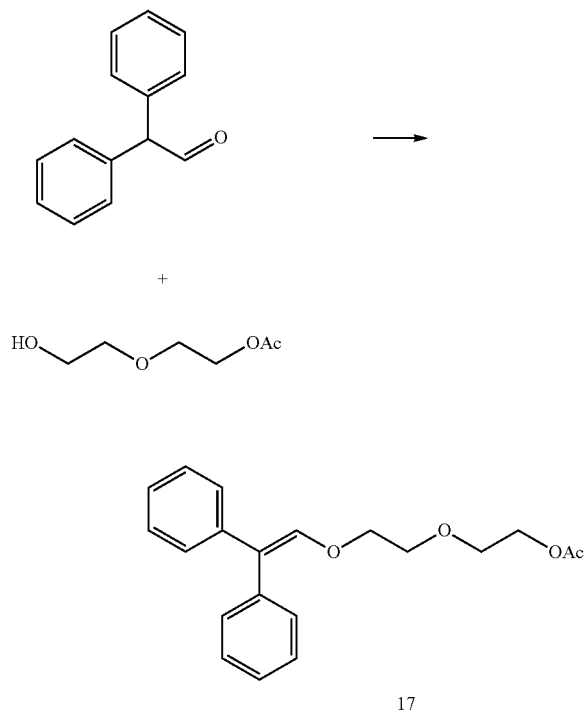 [SMILES: O=CC(c1ccccc1)c1ccccc1 ; CC(=O)OCCOCCO ; CC(=O)OCCOCCOC=C(c1ccccc1)c1ccccc1]

GC-MS (Instrument B) $t_R$: 18.69 min, 18.74 min, 18.90 min (Exact mass: 326.19 m/z, found: 326.2 m/z).

Example 18: Preparation of (2-((1-((1-methoxypropan-2-yl)oxy)propan-2-yl)oxy)ethene-1,1-diyl)dibenzene [18]

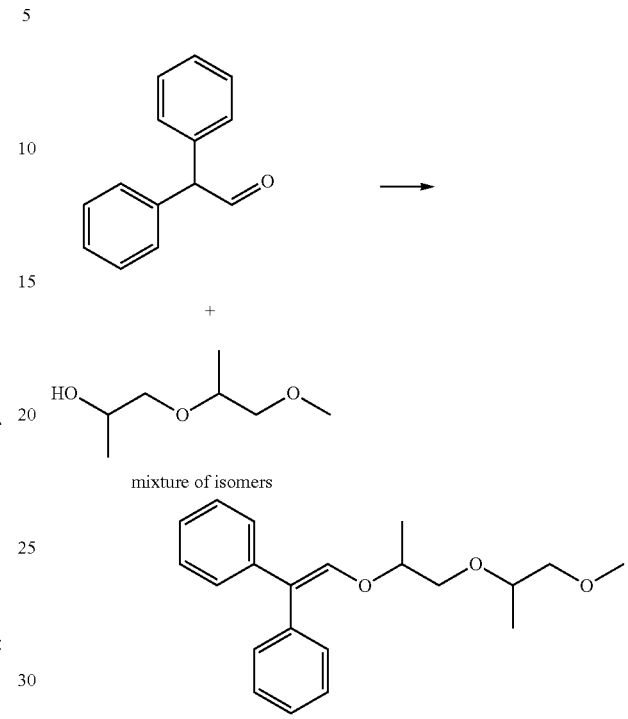

GC-MS (Instrument B) $t_R$: 18.69 min, 18.74 min, 18.90 min (Exact mass: 326.19 m/z, found: 326.2 m/z).

Example 19: Preparation of (E/Z)-1-(2-(2-(2-ethoxyethoxy)ethoxy)-1-phenylvinyl)-4-methylbenzene [19]

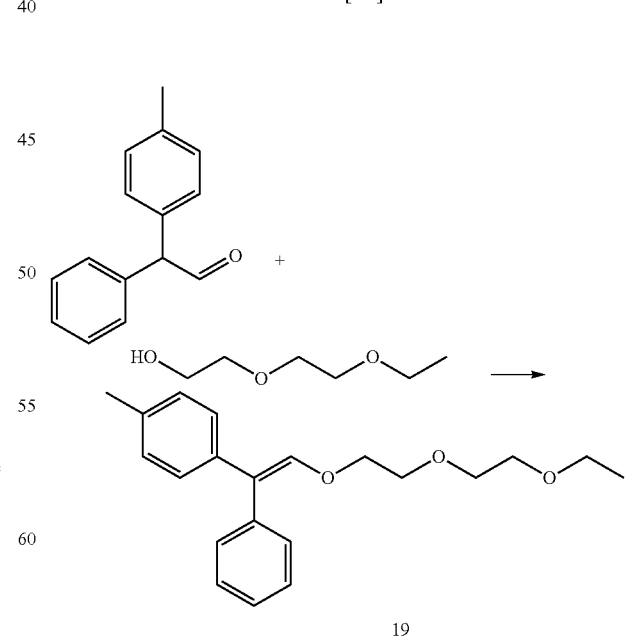

GC-MS (Instrument B) $t_R$: 19.94 min, 20.06 min (Exact mass: 326.19 m/z, found 326.3 m/z).

Example 20: Preparation of 4,4'-(2-(2-(2-ethoxyethoxy)ethoxy)ethene-1,1-diyl)bis(methylbenzene) [20]

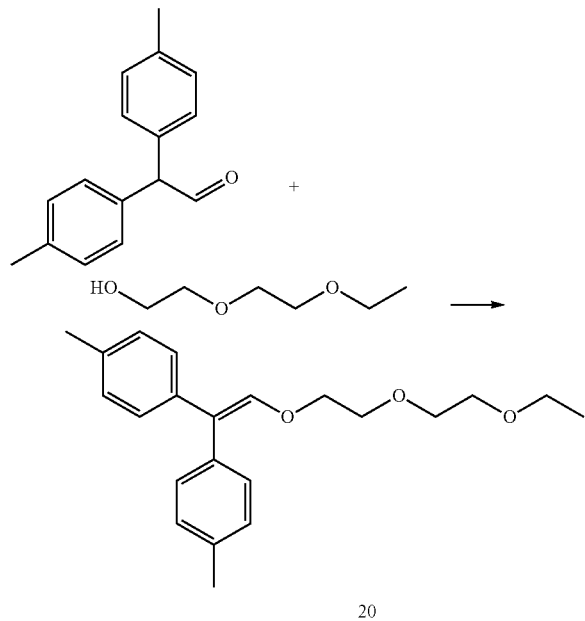

20

GC-MS (Instrument B) $t_R$: 20.95 min (Exact mass: 340.20 m/z, found: 340.3 m/z).

Example 21: Preparation of (E/Z)-1-methoxy-4-(2-((1-methoxypropan-2-yl)oxy)-1-phenylvinyl)benzene [21]

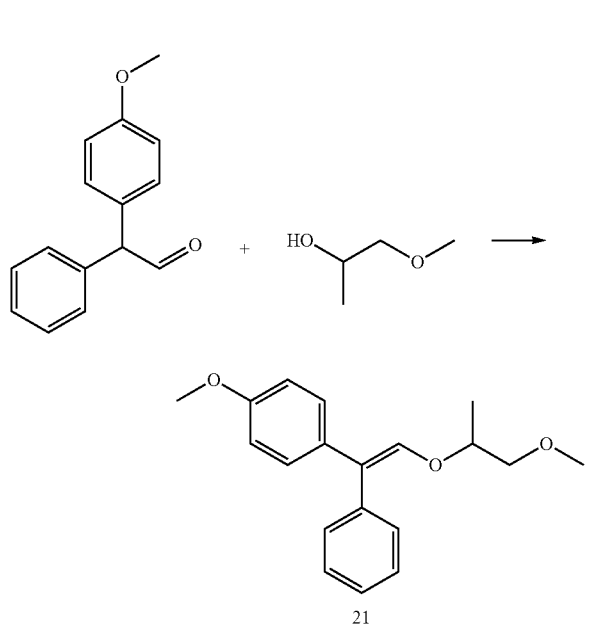

21

GC-MS (Instrument B) $t_R$: 18.58 min, 18.65 min (Exact mass: 298.16, found: 298.1 m/z).

Example 22: Preparation of (E/Z)-1-(2-(2-(2-ethoxyethoxy)ethoxy)-1-phenylvinyl)-4-methoxybenzene [22]

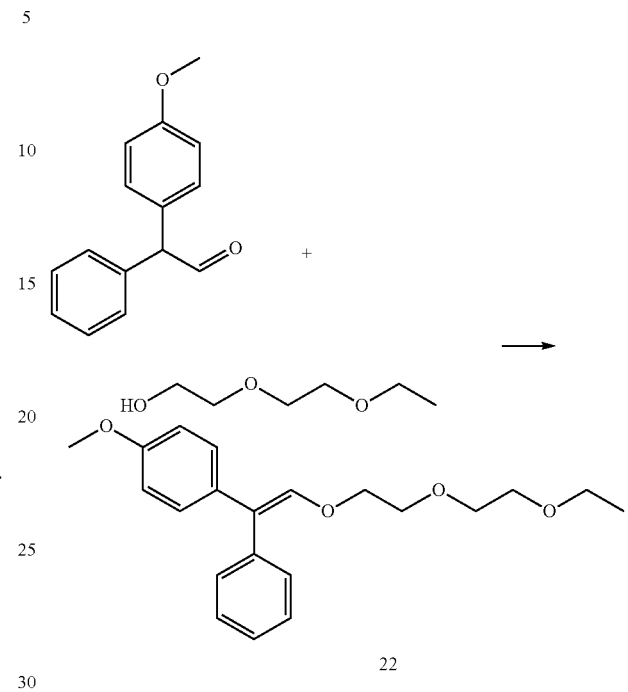

22

GC-MS (Instrument B) $t_R$: 21.17 min, 21.35 min (Exact mass: 342.18 m/z, found: 342.2 m/z).

Example 23: Preparation of (E/Z)-1-methoxy-4-(1-phenyl-2-(2-(2-propoxyethoxy)ethoxy)vinyl)benzene [23]

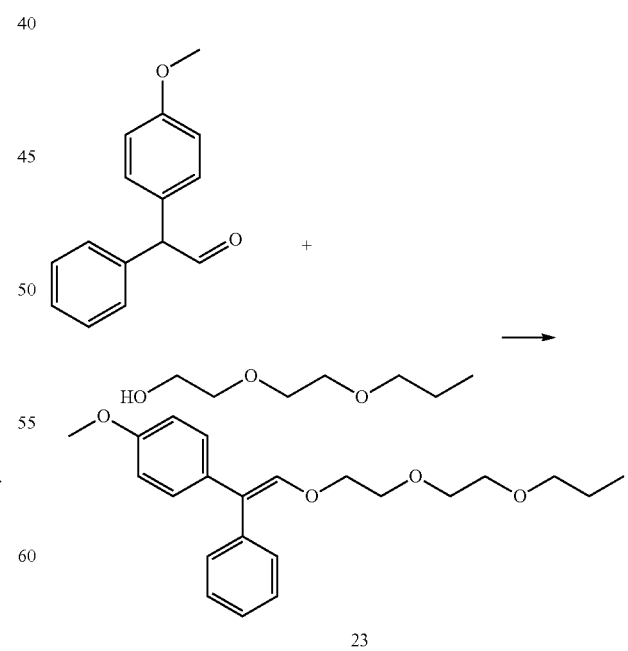

23

GC-MS (Instrument B) $t_R$: 22.51 min, 22.70 min (Exact mass: 356.20 m/z, found: 356.2 m/z).

Example 24: Preparation of (E/Z)-1-(2-(2-(2-butoxyethoxy)ethoxy)-1-phenylvinyl)-4-methoxybenzene [24]

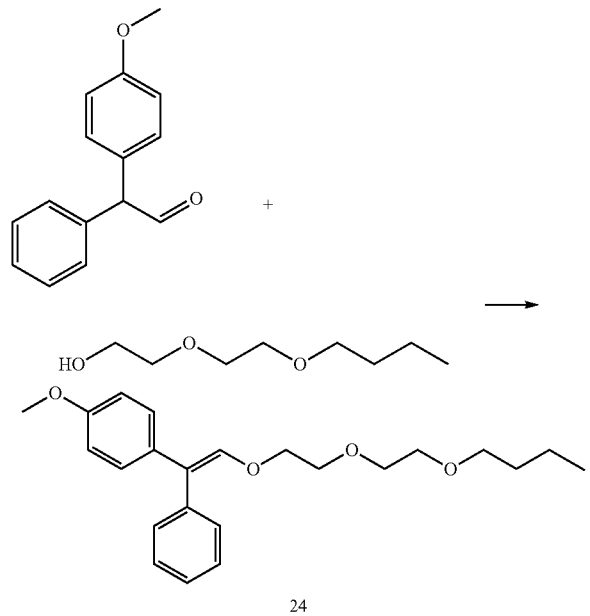

GC-MS (Instrument B) $t_R$: 23.91 min, 24.16 min (Exact mass: 370.21 m/z, found: 370.3 m/z).

Example 25a and 25b: a mixture of 1,1,14,14-tetraphenyl-3,6,9,12-tetraoxatetradeca-1,13-diene [25a] and 2-(2-(2-((2,2-diphenylvinyl)oxy)ethoxy)ethoxy)ethan-1-ol [25b]

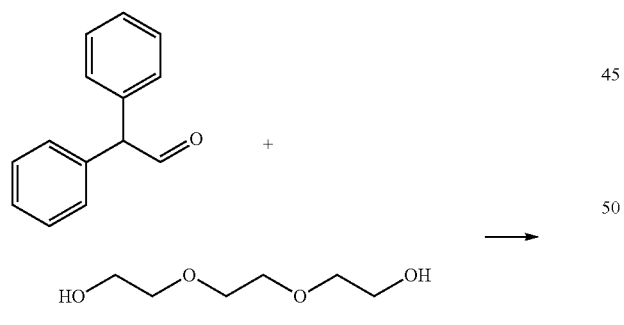

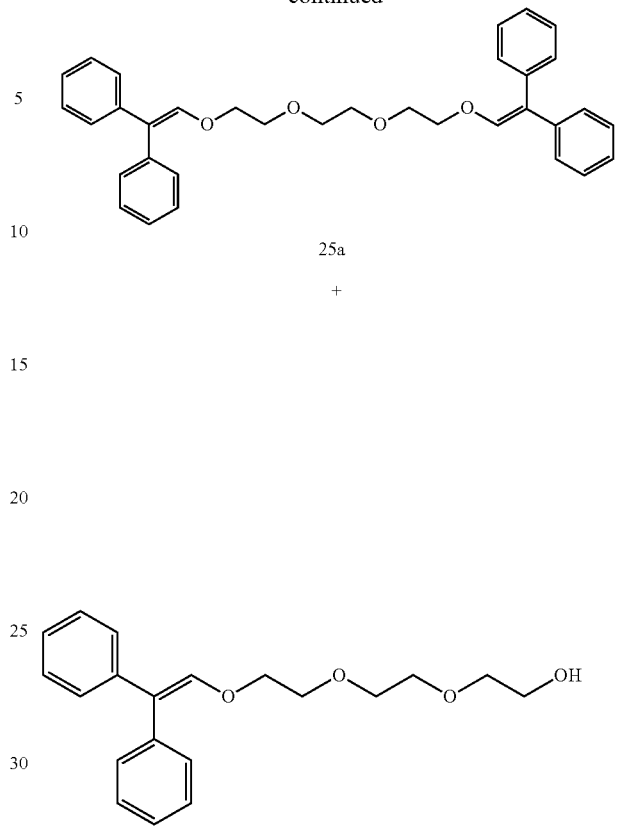

GC-MS (Instrument B) $t_R$: 21.68 min (Exact mass 25b: 328.17 m/z, found: 238.2 m/z), 58.24 min (Exact mass 25a: 506.25 m/z, found: 506.3 m/z).

Example 26a and 26b: Preparation of Example 26, a Mixture of (E/Z, E/Z) 2,15-bis(4-methoxyphenyl)-4,7,10,13-tetraoxahexadeca-2,14-diene [26a] and (E/Z)-2-(2-(2-((2-(4-methoxyphenyl)prop-1-en-1-yl)oxy)ethoxy)ethoxy)ethan-1-ol [26b]

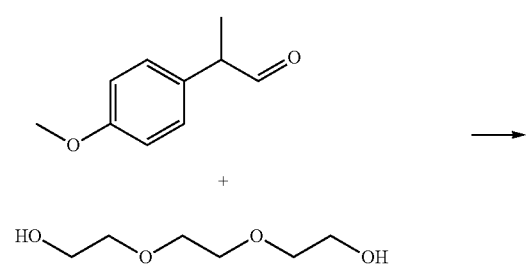

-continued

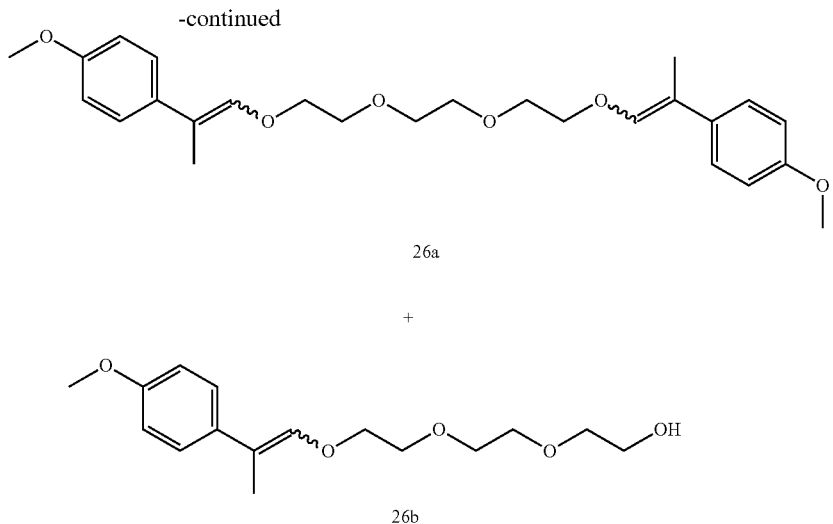

GC-MS (Instrument B) $t_R$: 19.88 min (26b—Exact mass: 296.2 m/z, found: 296.1 m/z), 42.99 min, 47.28 min, 52.19 min (26a—Exact mass: 442.2 m/z, found: 442.3 m/z), Unless noted otherwise, all examples described above are defined as non-VOC by ASTM D6886. This method uses MeP as a standard—if compound $t_R$>MeP $t_R$, compound is defined as non-VOC.

Instrument Parameters—Thermo ISQ GCMS (Instrument A)

Sample Prep: 100 μL sample diluted to 1 mL with toluene; Column: DB-5 30 m×0.25 mm×0.25 μm; Oven Ramp: 0-3 mins at 100° C.; Ramp 25 C/min to 280 C, Hold 15 mins; Injector: Temperature—300° C.; Split Flow—60; Carrier Flow Rate—1.4 mL/min; Volume—0.5 μL; MS: Transfer Line—280° C.; Ion Source Temp—250° C.; Mass Range—16-750 amu. Methyl palmitate $t_R$=8.67 min using the above method.

Instrument Parameters—Agilent 6890N GC with Agilent 5975B VL MSD (Instrument B)

Sample Prep: 100 μL sample diluted to 1 mL with toluene; Column: DB-5 30 m×0.25 mm×0.25 μm; Oven Ramp: 0-4.5 mins at 40° C.; Ramp 20 C/min to 280 C, Hold 53.5 mins; Injector: Temperature—250° C.; Split Flow—65 mL/min; Carrier Flow Rate—1.3 mL/min; Volume—1.0 μL; MS: Transfer Line—280° C.; Ion Source Temp—230° C.; Mass Range—34-700 amu. Methyl palmitate $t_R$=16.6 min using the above method.

The invention has been described in detail with reference to the embodiments disclosed herein, but it will be understood that variations and modifications can be effected within the spirit and scope of the invention.

We claim:

1. A compound according to Formula I:

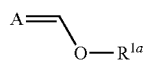

I wherein:

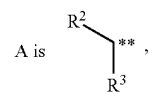

A is wherein ** indicates the point of attachment; and

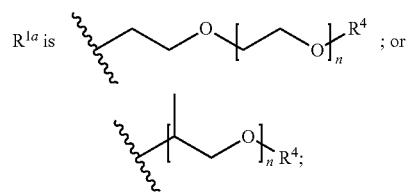

$R^{1a}$ is each $R^2$ is $(C_{4-10})$aryl each $R^3$ is $(C_{1-10})$alkyl or $(C_{4-10})$aryl;

$R^4$ is hydrogen, $(C_{1-12})$alkyl, $(C_{2-12})$alkenyl, or —C(O)$R^5$;

$R^5$ is $(C_{1-12})$ alkyl unsubstituted or substituted by $R^6$, $(C_{2-12})$ alkenyl unsubstituted or substituted by $R^6$, $(C_{3-8})$cycloalkyl, or 5- to 9-membered aryl;

$R^6$ is $(C_{1-4})$alkoxy, or oxo; and n is an integer from 1 to 15.

2. The compound of claim 1 wherein $R^2$ is phenyl, substituted phenyl, naphthyl, substituted napththyl, furanyl, or substituted furanyl.

3. The compound of claim 1 wherein $R^3$ is methyl, ethyl, propyl, butyl, pentyl, hexyl, heptyl, octyl, nonyl, decyl, phenyl, substituted phenyl, naphthyl, substituted napththyl, furanyl, or substituted furanyl.

4. The compound of claim 1 wherein n is an integer from 1 to 4.

5. The compound of claim 1 wherein $R^2$ is phenyl or substituted phenyl; $R^3$ is methyl, ethyl, phenyl, or substituted phenyl and n is an integer from 1 to 3.

6. A compound according to Formula II:

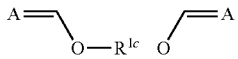

wherein: each A is independently

and
wherein ** indicates the point of attachment;

$R^{1c}$ is 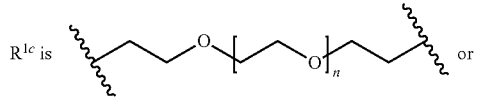 or

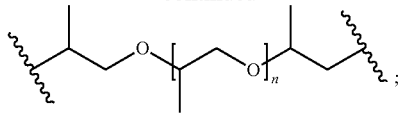

each $R^2$ is $(C_{4-10})$aryl;
each $R^3$ is $(C_{1-10})$alkyl or $(C_{4-10})$aryl; and
n is an integer from 1 to 15.

7. The compound of claim 6 wherein each $R^2$ is phenyl, substituted phenyl, naphthyl, substituted napththyl, furanyl, or substituted furanyl.

8. The compound of claim 6 wherein $R^3$ is methyl, ethyl, propyl, butyl, pentyl, hexyl, heptyl, octyl, nonyl, decyl, phenyl, substituted phenyl, naphthyl, substituted napththyl, furanyl, or substituted furanyl.

9. The compound of claim 6 wherein $R^2$ is phenyl or substituted phenyl, $R^3$ is methyl, ethyl, phenyl, or substituted phenyl and n is an integer from 1 to 3.

10. An enol ether compound selected from the group consisting of compounds 1-3, 4(a), 4(b), 5(a), 5(b), 6-24, 25(a), 25(b), 26(a) and 26(b):

1

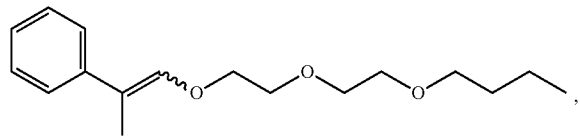

2

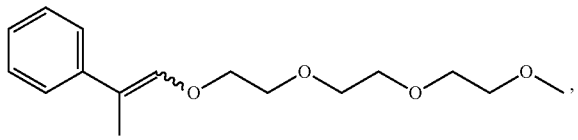

3

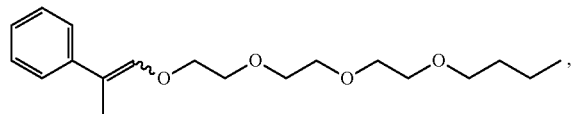

4a

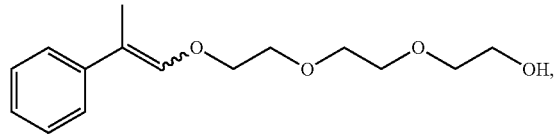

4b

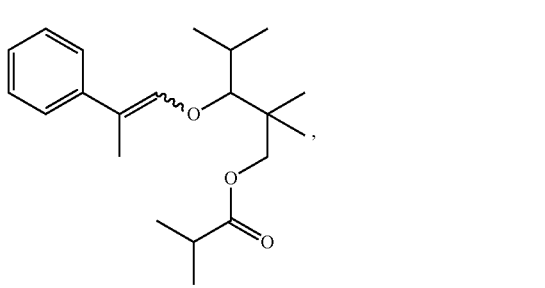

5a

5b

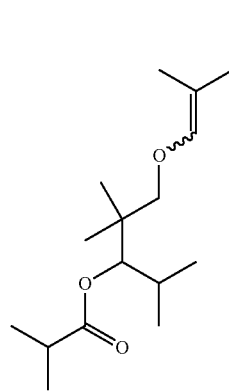

6

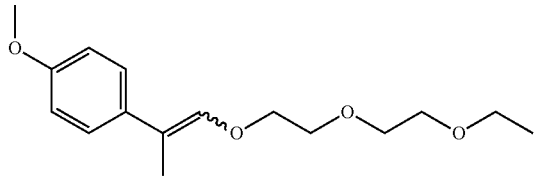

-continued
7
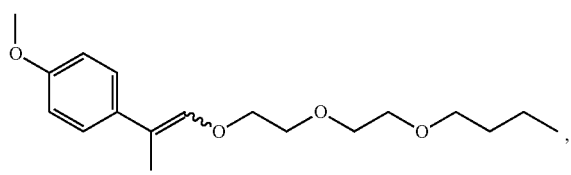
8
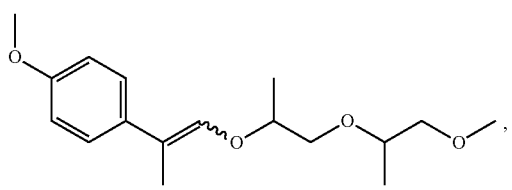
9
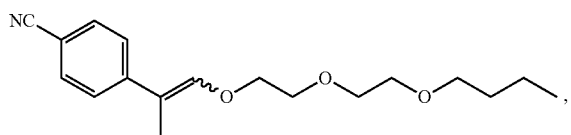
10
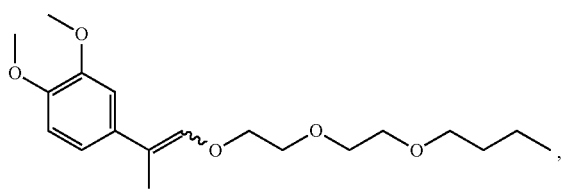
11
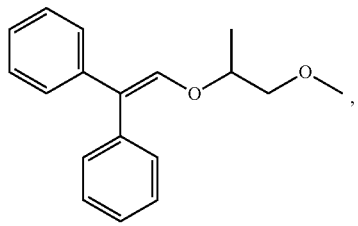
12
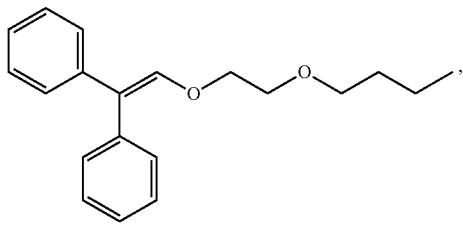
13
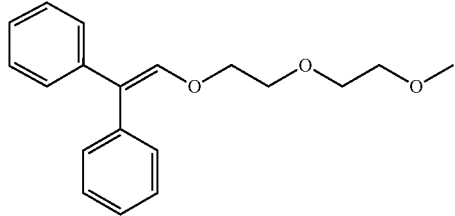
14
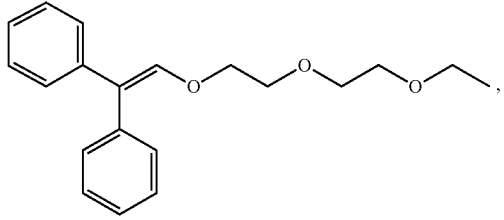
15
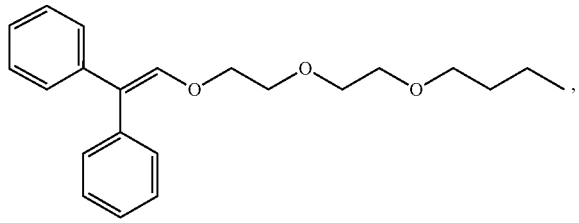
16
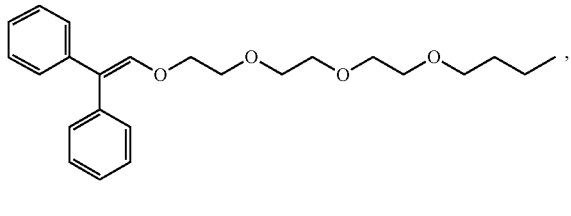
17
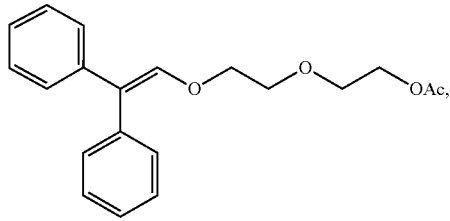
18
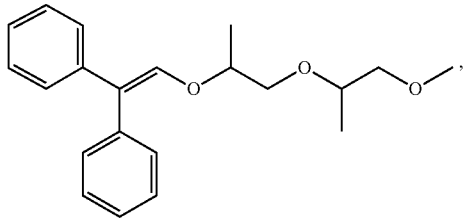
19
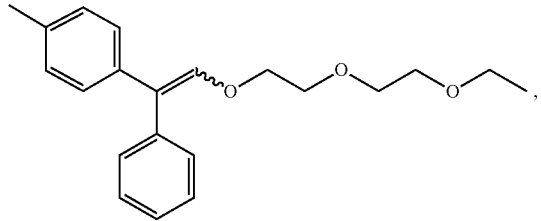
20

-continued
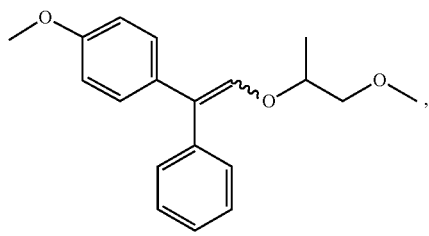
21
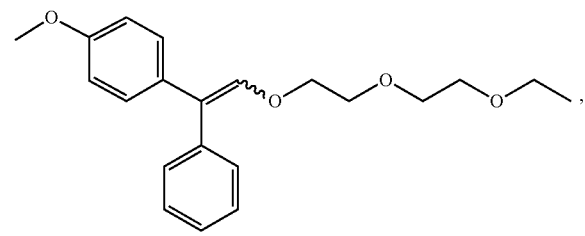
22
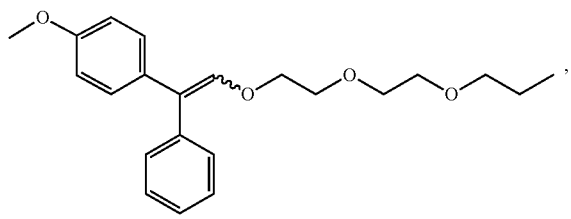
23
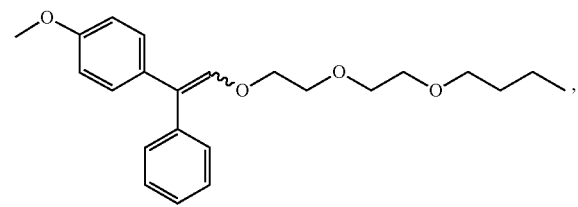
24
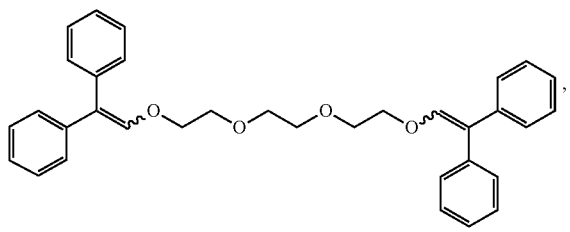
25a
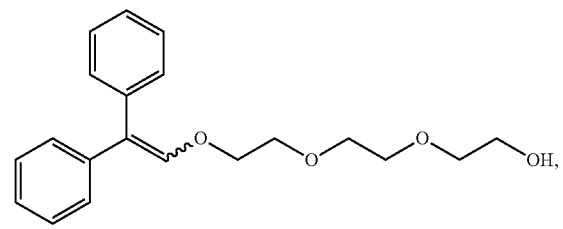
25b
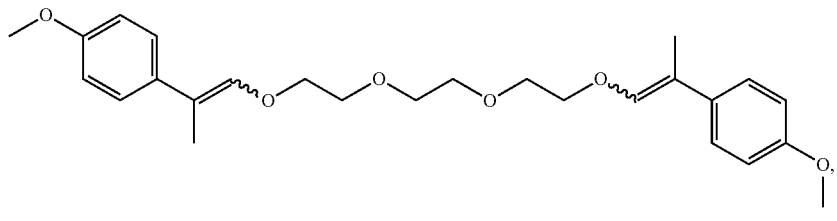
26a
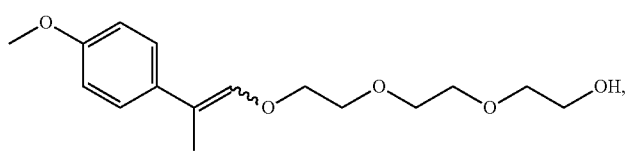
26b
and isomers thereof.
* * * * *